(12) United States Patent
Gundlapalli

(10) Patent No.: US 8,070,763 B1
(45) Date of Patent: Dec. 6, 2011

(54) DISPOSABLE ORAL HYGIENE INSTRUMENT AND METHODS AND PACKAGES FOR SAME

(76) Inventor: Ramarao V. Gundlapalli, Leesburg, IN (US)

( * ) Notice: Subject to any disclaimer, the term of this patent is extended or adjusted under 35 U.S.C. 154(b) by 1395 days.

(21) Appl. No.: 10/300,176

(22) Filed: Oct. 22, 2004

Related U.S. Application Data

(63) Continuation of application No. 10/282,643, filed on Oct. 29, 2002, now abandoned.

(60) Provisional application No. 60/339,086, filed on Oct. 30, 2001.

(51) Int. Cl.
*A61B 17/24* (2006.01)

(52) U.S. Cl. .......................................... 606/161

(58) Field of Classification Search .......... 606/160–163; 132/321, 323, 329; 206/63.5, 820
See application file for complete search history.

(56) References Cited

U.S. PATENT DOCUMENTS

| | | | |
|---|---|---|---|
| D253,789 S | 12/1979 | Gupta | |
| D259,209 S | 5/1981 | Gautama | |
| 4,270,556 A * | 6/1981 | McAllister | 132/321 |
| D265,270 S | 7/1982 | McCarty | |
| D267,508 S | 1/1983 | Gupta | |
| 4,455,704 A | 6/1984 | Williams | |
| D281,720 S | 12/1985 | Tiwari | |
| 4,582,059 A | 4/1986 | Tiwari | |
| D283,952 S | 5/1986 | Berkowitz | |
| D285,250 S | 8/1986 | Audette | |
| D285,251 S | 8/1986 | Audette | |
| D285,252 S | 8/1986 | Audette | |
| D285,253 S | 8/1986 | Audette | |
| D285,341 S | 8/1986 | Audette | |
| D285,342 S | 8/1986 | Audette | |
| 4,610,043 A | 9/1986 | Vezjak | |
| D286,326 S | 10/1986 | Gautam | |
| D299,055 S | 12/1988 | Swamy | |
| D303,289 S | 9/1989 | Swamy | |
| 5,061,272 A | 10/1991 | Reese | |
| D326,324 S | 5/1992 | Iida | |
| 5,217,475 A | 6/1993 | Kuber | |
| 5,226,197 A | 7/1993 | Nack | |

(Continued)

OTHER PUBLICATIONS

Rosenberg, Mel; The Science of Bad Breath, Scientific American, Apr. 2002, p. 73.

*Primary Examiner* — Kevin T Truong
(74) *Attorney, Agent, or Firm* — James A. Gavney, Jr.; JAG Patent Services LLC

(57) ABSTRACT

Described are packages and systems for conveniently dispensing tongue cleaning devices. The packages include containers containing a plurality of tongue cleaning devices. The package and devices are arranged in such a fashion that the tongue cleaning devices are presented individually for dispensing from the container. Arrangements for achieving convenient dispensing include strips containing a plurality of tongue cleaning devices attached to one another and wound around a spindle within the container. The strip exits an opening in the container and conveniently presents devices sequentially which can be separated from one another at relatively weak points along the strip and/or using cutting elements on the container. Additional embodiments include a plurality of tongue cleaning devices in a stacked relationship in a container, and presented individually for sequential dispensing from the container. The invention provides packages, articles of manufacture and tongue cleaning devices which can be conveniently stored, used, and transported, and which are readily adapted as disposable items thus avoiding the need for cleaning and storing operations of conventional non-disposable tongue cleaners.

19 Claims, 6 Drawing Sheets

U.S. PATENT DOCUMENTS

| | | |
|---|---|---|
| D338,084 S | 8/1993 | Potti |
| D350,202 S | 8/1994 | Kashani |
| D354,624 S | 1/1995 | Gupta |
| D376,695 S | 12/1996 | Tveras |
| D377,417 S | 1/1997 | Gupta |
| D378,411 S | 3/1997 | Taoatao |
| 5,613,262 A | 3/1997 | Choy-Maldonado |
| 5,656,014 A | 8/1997 | Rooney |
| D384,153 S | 9/1997 | Potti |
| D384,744 S | 10/1997 | Sharma |
| D389,579 S | 1/1998 | Faddis |
| D392,386 S | 3/1998 | Nguyen |
| 5,735,864 A | 4/1998 | Heisinger, Jr. |
| D394,705 S | 5/1998 | Gupta |
| 5,766,193 A | 6/1998 | Millner |
| D396,288 S | 7/1998 | Samuel |
| 5,792,159 A | 8/1998 | Amin |
| 5,810,856 A | 9/1998 | Tveras |
| 5,817,114 A | 10/1998 | Anderson |
| 5,842,247 A | 12/1998 | Decesare |
| D404,130 S | 1/1999 | Stefano |
| 5,868,769 A * | 2/1999 | Rosenblood et al. ......... 606/161 |
| D406,341 S | 3/1999 | Stefano |
| D406,342 S | 3/1999 | Stefano |
| 5,893,860 A | 4/1999 | Ripich |
| 5,916,228 A | 6/1999 | Ripich |
| D411,884 S | 7/1999 | Dewti |
| 5,928,254 A | 7/1999 | Jensen |
| D412,986 S | 8/1999 | Abraham |
| 5,938,673 A | 8/1999 | DePierro |
| 5,947,132 A * | 9/1999 | Swanson ....................... 132/321 |
| 5,967,152 A | 10/1999 | Rimkus |
| 5,979,005 A | 11/1999 | Lecce |
| 5,980,541 A | 11/1999 | Tenzer |
| 5,980,542 A | 11/1999 | Saldivar |
| 5,984,935 A | 11/1999 | Welt |
| 6,013,089 A | 1/2000 | Goldberg |
| 6,015,293 A | 1/2000 | Rimkus |
| D420,742 S | 2/2000 | Noble |
| 6,019,773 A | 2/2000 | Denmark |
| D427,310 S | 6/2000 | Haneiph |
| 6,102,923 A | 8/2000 | Murayama |
| 6,152,939 A * | 11/2000 | Nguyen et al. ................ 606/161 |
| 6,159,226 A | 12/2000 | Kim |
| 6,171,323 B1 | 1/2001 | Potti |
| 7,055,530 B2 * | 6/2006 | Husted .......................... 132/321 |

* cited by examiner

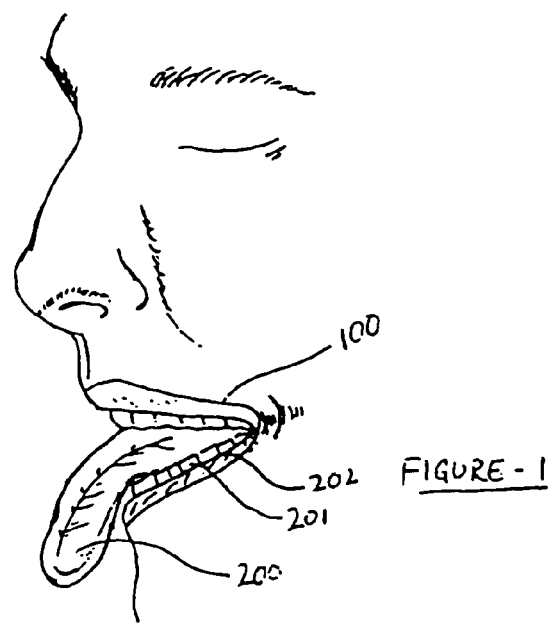
FIGURE-1
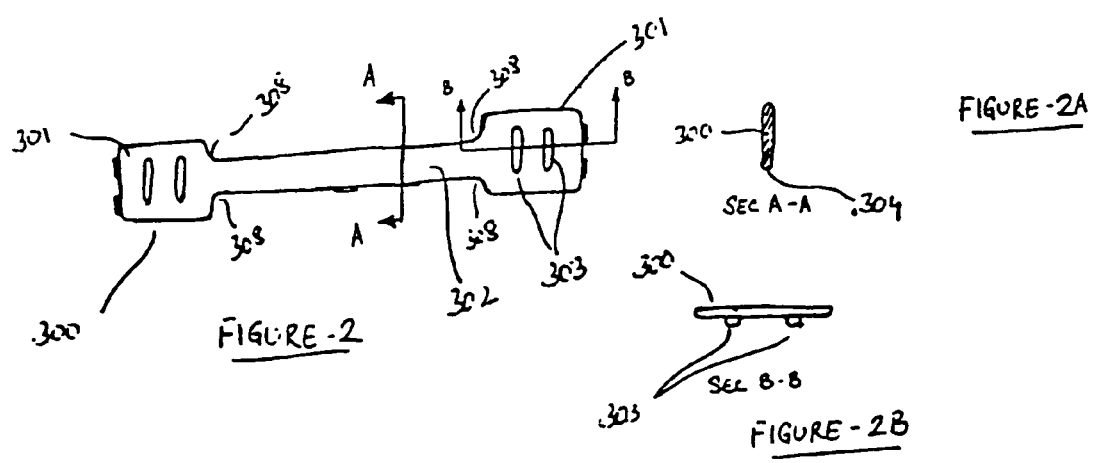
FIGURE-2
FIGURE-2A
FIGURE-2B

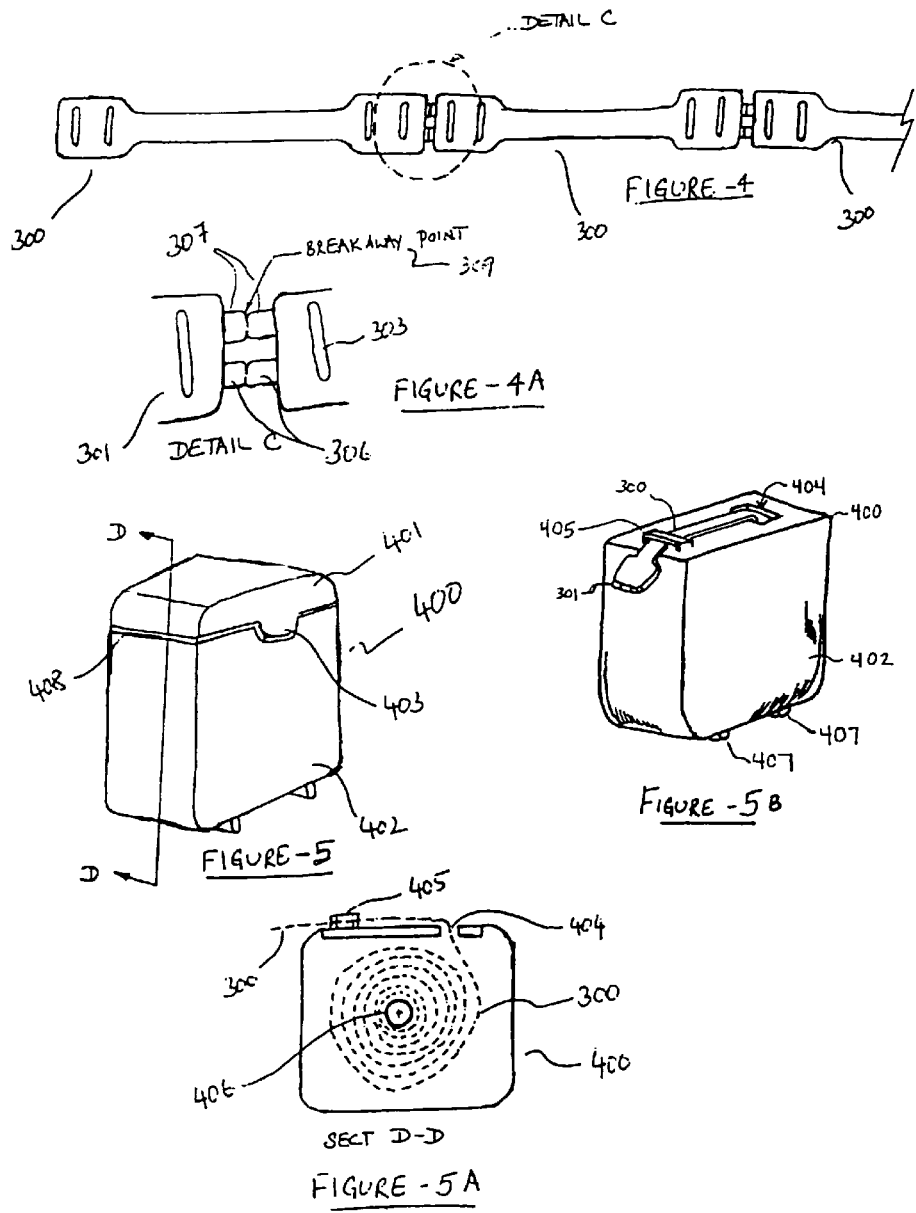

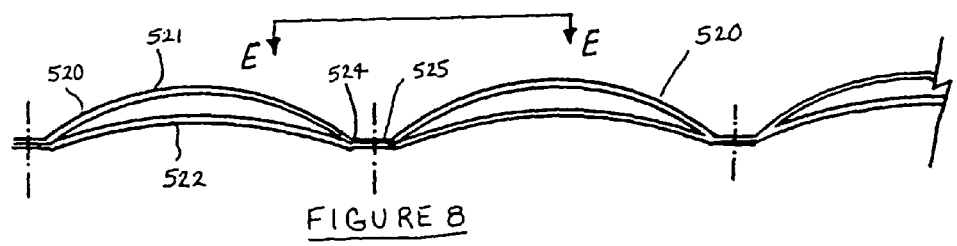
FIGURE 8
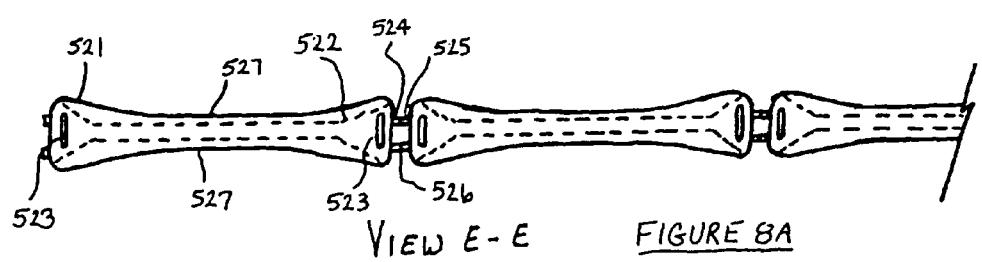
VIEW E-E          FIGURE 8A

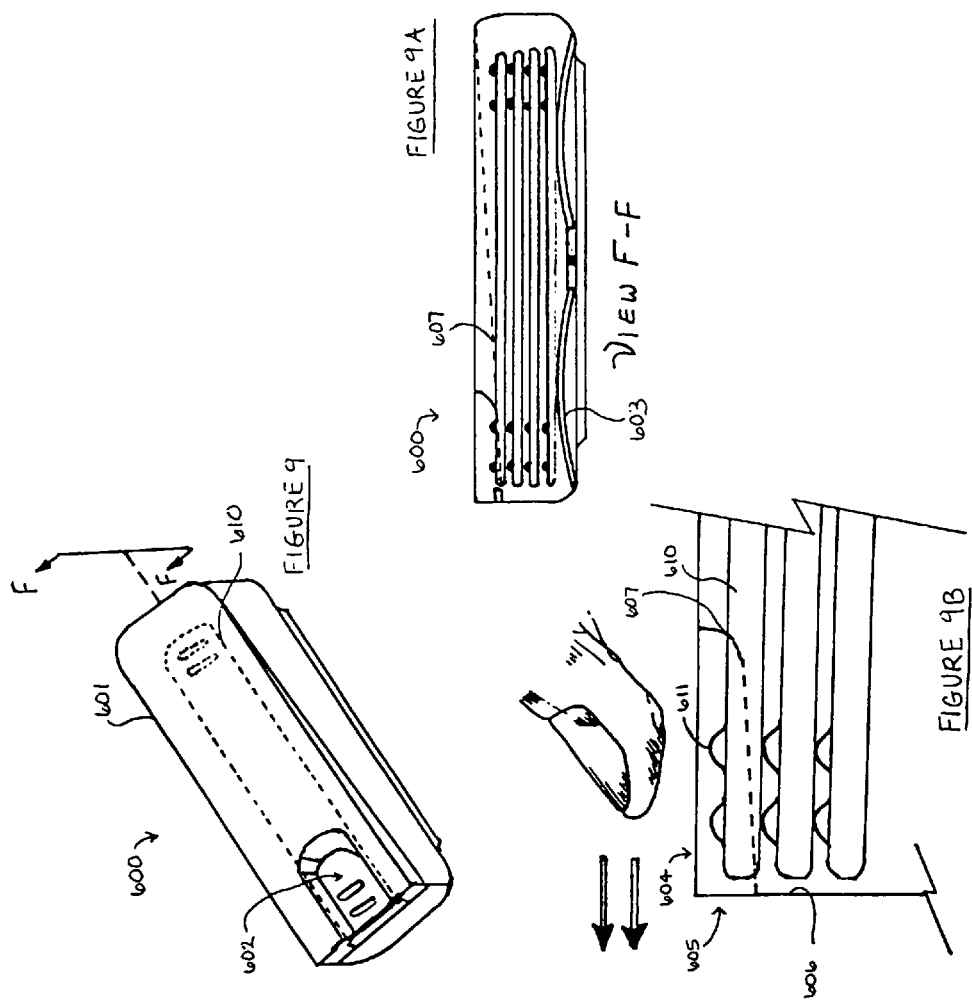

DISPOSABLE ORAL HYGIENE INSTRUMENT AND METHODS AND PACKAGES FOR SAME

REFERENCE TO RELATED APPLICATIONS

The present application is a continuation of the U.S. patent application Ser. No. 10/282,643 filed Oct. 29, 2002 now abandoned entitled DISPOSABLE ORAL HYGIENE INSTRUMENT AND METHODS AND PACKAGES FOR SAME, which claims the benefit of U.S. Provisional Patent Application, Ser. No. 60/339,086 filed Oct. 30, 2001, each of which is hereby incorporated by reference in its entirety.

TECHNICAL FIELD OF THE INVENTION

The present invention relates generally to methods and devices for facilitating maintenance of good oral hygiene. More particularly, the present invention is related to novel instruments for maintaining oral hygiene, and packages and methods for storing and dispensing such instruments.

BACKGROUND OF THE INVENTION

As further background, conventional oral hygiene practices are designed to protect and maintain in good health and condition three main components—the teeth, gums, and tongue. Brushing one's teeth has become a fairly routine practice in society, with medium to soft bristle brushes being recommended along with toothpaste to remove plaque and food particles on and in between the teeth and gums. Although perhaps less widely practiced, the use of dental floss to clean between the teeth and gums is also a common practice. Current recommendations include such use of dental floss at least once daily to help remove materials which may cause tooth decay and a consequent need for treatment.

Dental practitioners recommend the use of a regular toothbrush with paste to brush the tongue. In addition, tongue cleaners are available and are used to scrape debris from the tongue as a separate practice from regular brushing and flossing. Nonetheless, tongue cleaning is perhaps the least practiced of these oral hygiene components. It is currently estimated that only one out of ten individuals clean their tongues each day.

The tongue serves multiple purposes in the mouth including to taste, to transfer food between teeth during chewing, and to participate in speech. In the course of daily eating habits a distinctive layer of plaque, bacteria, tongue debris or other material builds on the tongue. Excessive plaque can interfere with taste, and cause bad breath. Mouthwash and mouth fresheners may help to reduce bad breath but they do not eliminate the root cause. Improved habits and devices are thus needed to eliminate that root cause—tongue plaque. While a substantial percentage of the population may attempt to use a toothbrush to clean their tongue, the toothbrush is not designed for this purpose. The flexible bristles on the toothbrush do not provide sufficient resistance to effectively scrape away plaque on the tongue. In addition, the motion provided by the user may not be sufficiently symmetric about the tongue to cover most of its area. Moreover, the use of a toothbrush to clean the tongue can lead to choking or gagging, especially in children and adolescents.

While instruments have been proposed that are especially adapted for tongue cleaning, they have typically been inconvenient to use, to clean, and to store. Thus there exist needs for improved tongue cleaning instruments which are convenient to use, store and dispense. The present invention is addressed to these needs.

SUMMARY OF THE INVENTION

Accordingly, in one aspect, the present invention provides a package for dispensing devices for cleaning tongue surfaces. The package includes a container having an opening, and a plurality of devices disposed within the container, wherein the devices each include at least one edge adapted to clean tongue surfaces. In accordance with this aspect of the invention, the devices are connected to one another, but are separable from one another at breakaway points in between individual ones of the devices. These devices are dispensable through the opening in the container.

Another embodiment of the invention provides an article of manufacture that includes a strip having a plurality of devices for cleaning tongue surfaces, wherein the devices each have at least one edge adapted to clean tongue surfaces. The devices are separable from one another at breakaway points on the strip that occur in between individual ones of the devices.

In another embodiment, the invention provides a device for cleaning tongue surfaces that includes a central portion having at least one edge adapted to clean tongue surfaces. The device includes a first grip portion at a first end of the central portion, and a second grip portion at a second end of the central portion. The first and second grip portions each have a surface having proturbences therefrom to facilitate gripping during use. The central portion of the device is in a curved condition, or is deformable to a curve condition by manipulation of the first and second grip portions.

Another embodiment of the invention relates to a package for dispensing devices for cleaning tongue surfaces. The package includes a container having an opening, and a strip disposed in the container and containing a plurality of devices for cleaning tongue surfaces. Each of the devices has at least one edge adapted to clean tongue surfaces. The strip is dispensable through the opening, and the package includes a cutting element arranged for cutting the strip to separate devices from the strip.

In another embodiment, the present invention provides a package for dispensing devices for cleaning tongue surfaces. The package includes a container having an opening. A plurality of devices for cleaning tongue surfaces is disposed in the container, wherein each device has at least one edge adapted to clean tongue surfaces. The devices are dispensable through the opening and are arranged in the container in a fashion wherein dispensing a first device from the opening presents a second device at the opening for subsequent dispensing.

The present invention provides improved tongue cleaning devices, articles of manufacture, packages for dispensing tongue cleaning devices, and related methods. Additional features, advantages and embodiments of the invention will be apparent from the further descriptions herein.

BRIEF DESCRIPTION OF THE FIGURES

FIG. 1 provides an elevational view of the face of an individual with an extended tongue typical during a cleaning process.

FIG. 2 provides a front view of a tongue cleaning device of the invention.

FIG. 2A provides a cutaway view taken along line A-A of FIG. 2.

FIG. 2B provides a cutaway view of the device of FIG. 2 taken along line B-B.

FIG. 4 provides a front view of a strip containing a plurality of tongue cleaning devices of FIG. 2 interconnected by breakaway tabs.

FIG. 4A provides an enlarged cutaway view of the breakaway tabs as depicted in FIG. 4.

FIG. 5 provides a perspective view of a package for dispensing tongue cleaners in accordance with the invention.

FIG. 5A provides a cross-sectional view of the package of FIG. 5 (with the cap cut away) taken along the plane of line D-D and viewed in the direction of the arrows.

FIG. 5B provides a cutaway view of the package of FIG. 5 having the lid portion removed.

FIG. 8 shows a side view of a strip of tongue cleaning devices each having a loop structure.

FIG. 8A shows a top view of the strip of tongue cleaning devices of FIG. 8.

FIG. 9 provides a perspective view of another package for dispensing tongue cleaners of the invention.

FIG. 9A shows a cross sectional view of the package of FIG. 9 taken along the axial plane defined by line F-F and viewed in the direction of the arrows.

FIG. 9B provides an enlarged cutaway view of the opening of the package of FIG. 9 during a dispensing operation.

DETAILED DESCRIPTION OF THE PREFERRED EMBODIMENTS

Figure 3:
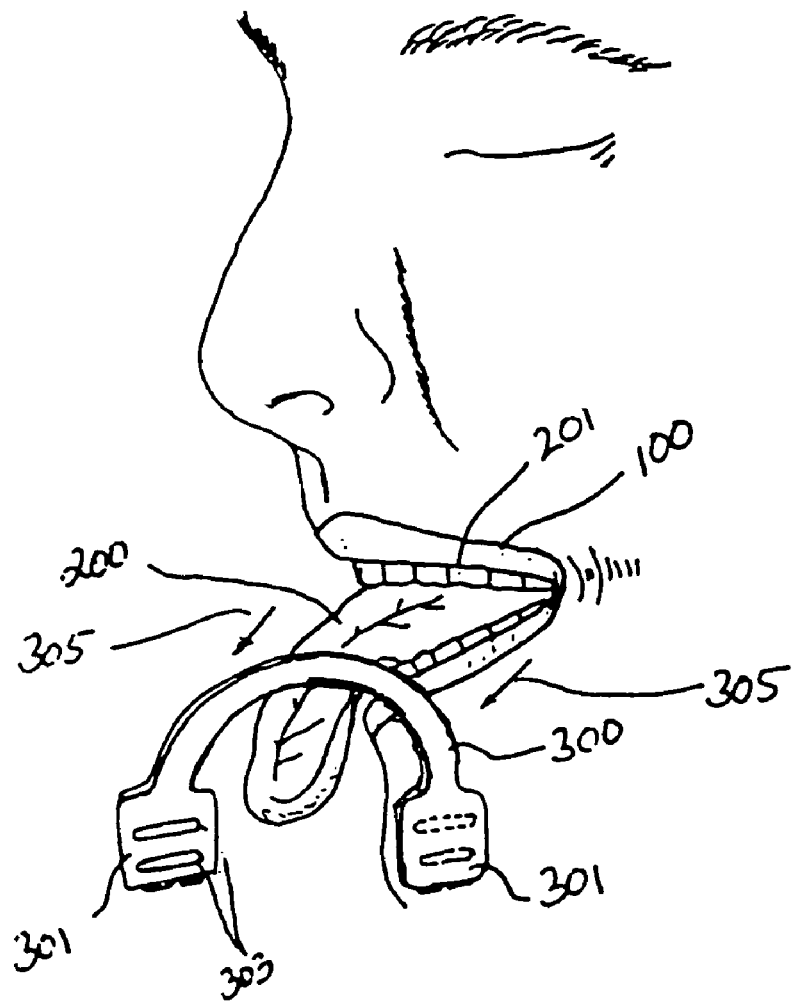
FIG. 3 provides a perspective view of a tongue cleaning device of the invention in use to clean the tongue.

For the purposes of promoting an understanding of the principles of the invention, reference will now be made to the embodiment illustrated in the drawings and specific language will be used to describe the same. It will nevertheless be understood that no limitation of the scope of the invention is thereby intended, and alterations and modifications in the illustrated device, and further applications of the principles of the invention as illustrated therein are herein contemplated as would normally occur to one skilled in the art to which the invention relates.

As disclosed above, the present invention provides novel tongue cleaning devices, and systems, packages and related methods for dispensing them. The devices and packages of the invention are conveniently used and allow for disposability, easy storage and portability during travel.

With reference now to FIG. 1, shown are details of an individual's face with tongue extended in a position typical of a cleaning operation. The individual includes a mouth 100 through which solid and liquid nutrients are consumed. The mouth 100 includes several anatomical sites including the tongue 200, teeth 201, and the gums 202. These three parts of the mouth are the most important in terms of oral hygiene. While the shape of the tongue may vary from individual to individual, its main features include the dorsum or upper surface of the tongue body, and the cecum, from which the thyroid gland originates. The dorsum of the tongue has several types of papillae bearing numerous taste buds. These are usually arranged in a V-shape. One type of papillae, called the fungiform papillae, also contains numerous taste buds which help to identify taste, touch, pain and temperature of any materials touching the same. To optimize the sense of taste, touch, pain and temperature, the papillae must be clean and free from plaque deposits that may form during normal eating habits.

With reference now to FIG. 2, shown is a tongue cleaning device 300 of the invention. The device 300 has two ends 301 which may or may not be identical to one another. The device 300 further includes a body or central portion 302 connected to the end portions 301 by a neck region 308. In accordance with the invention, neck region 308 can be either a sharp transition or a gentle radius as shown in the illustrated embodiment. In certain embodiments, the ends 301 are wider than the central portion of the body 302. The ends 301 are used as handles during use of the device 300. Further, ends 301 may have extrusions, protrusions or other proturbences 303 on either one end or on both ends 301. The proturbences facilitate gripping by a user of the device, for example between the index finger and the thumb. Such surface gripping features assist in maintaining the user's grasp of the device during an operation wherein the body or central portion 302 is passed over the tongue in a scraping motion. In certain embodiments of the invention, typical dimensions of the device 300 and similar devices described herein are about 100 millimeters to about 125 millimeters (i.e. about four inches to about five inches) in total length, about 5 millimeters (i.e. about 0.2 inches) in breadth along the central portion 308, and less than about 1 millimeter in width (thickness), for example about 0.5 millimeters (i.e. about 0.02 inches) in width. The breadth of the ends or handle portions 301 may be the same as, or vary from, the breadth of the central portion 302. Preferably, the breadths of the end portions 301 will be greater than that of the central portion 302. It will be understood that these dimensions are illustrative of preferred embodiments and that the dimensions of devices of the invention may vary as determined by ergonomics, manufacturing concerns, and other similar factors.

With reference now to FIG. 2 along with FIGS. 2A and 2B, as discussed above, the handles 301 desirably include gripping surface features such as extrusions or protrusions 303 or other proturbences. It will be understood that the depicted handles 301 and protrusions or extrusions 303 are illustrative in nature, and that they need not be symmetrical about the body or central portion 302 of the device 300 in accordance with the invention. Such extrusions can be of linear, cross-hatched, oblique or curved design, or any other pattern or configuration that provides for the grip needed between the index finger and the thumb to help in the scraping motion when the device 300 is used on the tongue. Additionally, other gripping features on handle portions of the devices may include non-skid laminations or secondary layers adhered to the handle surface, optionally using bonding agents such as medical grade glue.

With reference particularly to FIG. 2A, shown is a cross-sectional view of the body or central portion 302 of the device 300. The central portion 302 presents two edges which are configured to be smooth to help prevent injury to the tongue during use of the device 300. At the same time, at least one of these edges is radiused or otherwise adapted to present an edge that is effective in scraping debris from tongue surfaces. In one embodiment, both edges of the central portion 302 can be so adapted.

Generally, tongue cleaning devices of and used in packages and systems of the invention will be free of any sharp edges or corners that could cause injury to tongue or other tissues during handling and use. Tongue cleaning devices of and used in the invention can be made of any suitable biocompatible material having a ductility and yield strength sufficient to prevent breakage during use, including for example a plastic (e.g. a soft plastic such as silicone) or metal that is not susceptible to rust. If made of plastic, devices of the invention may be manufactured in various colors and designs. Further, plastic used in tongue cleaning devices of the invention can be impregnated or coated with flavoring agents such as mint, spearmint, bubblegum, fruit flavors, etc., and/or with coloring agents, including the provision of varying color, art design, or patterns on the device, to make the device more appealing to adult, adolescent or child users.

With reference now to FIG. 3, shown is device 300 of the invention in use. In particular, device 300 is used in a scraping operation upon the tongue. Typically, the device 300 will be used to scrape the tongue in a top to bottom (or back to front) fashion as indicated by arrows 305. The body or central portion 302 of the device 300 may be deformed to a curved condition across the tongue using the handles 301. As shown in FIG. 3, the tongue is extended out from the mouth in a generally flat position, which allows for more complete scraping of the tongue with the central portion 302. One or more scraping motions from top to bottom are performed to remove debris. The number of scraping motions or repetitions required may depend upon the duration between cleaning of the tongue and the kinds of foods that the individual eats or drinks, as excessively fatty foods may build plaque quicker than other foods. It is expected that at least three such motions will at times be needed to help remove plaque buildup on the tongue. Lesser repetitions may be used if a regular tongue scraping habit is developed. The result of good scraping is evidenced by the exposure of the underlying pink tissue of the tongue and the exposure of the taste buds contained in the numerous papillae on the tongue. The device 300 of the invention can be effectively used to clean substantial portions of the tongue without choking or other difficulties such as gagging, with trial and error by the user establishing the most effective and comfortable range of tongue cleaning. For children or adolescents, some supervision may be needed until safe and comfortable habits are established.

With continued reference to FIG. 3, the illustration assists in understanding the effective design of the device 300. As can be seen, central portion 302 is curved over and in contact with the tongue for effective scraping. Central portion 302 is of sufficient length to traverse the tongue and as shown is desirably sufficiently long to space handles 301 from the tongue for effective gripping by the user. After an initial scraping of the tongue, the user can rinse the invention with water, optionally soapy water, and then use the device again for continued cleaning of the tongue. In addition, the device 300 may be inverted to use the opposite edge of the central portion 302 in similar fashion for tongue cleaning. The device 300 may then be disposed of after the cleaning operation is complete.

Referring now to FIG. 4, shown is an article of manufacture including a strip containing multiple devices 300 of the invention. The strip may contain, for example, fifteen or thirty devices 300, which can thereby be packaged together. It will be understood that the number of devices in the strip or otherwise packaged together may vary and that systems containing two or more devices for tongue cleaning are considered as within the broader aspects of the invention.

With reference to FIG. 4A, the devices 300 are attached in sequence by two or more slender filaments 307 on the end of a first device 300 and two or more slender filaments 306 on an end of a second device 300, with the filaments made of the same material as the devices 300. The filaments 306 and 307 extend from the end of one device handle 301 to the end of another device handle 301. Intentional notches 309, providing breakaway points, are made on the slender filaments 306 and 307. The filaments 306 and 307 are designed such that there is a predetermined force to failure of the filaments at the notched area 309. This force to failure helps the user to separate one device of the invention 300 from the remaining devices of the invention in the strip. These notched and other breakable areas that are relatively weaker against breakage than adjacent areas are contemplated for use in the present invention, including for example thinned wall areas, perforations, scores, or the like.

As explained below, a dispensing packaging system for the devices may also include an adaptation to aid in the separation of devices 300 from one another. In the illustrated embodiment, the filaments 306 and 307 are manufactured as a part of the devices 300 and in particular the handles 301. Other methods of attachment of devices 300 to one another such as removable glue, static attachment, etc., are also contemplated as within the present invention, wherein such attachments can be similarly used in the convenient sequential dispensing or presentation of devices from packages.

FIG. 5 provides a perspective view of a container or package 400 providing a dispensing system for devices for cleaning tongue surfaces. The container or package 400 contains features including a lid 401, body 402, lid handle 403, closure rim 408, and standing legs 407. Lid 401 allows the container to be opened and closed as needed, which operation is facilitated by the lid handle 403. Lid 401 helps to prevent dust and other debris from entering and contaminating the devices 300 stored within the container 400. Lid 401 interacts with the body 402 and in particular the closure rim 408 to create a closure seal for such purposes. The standing legs 407 may be provided in any number or configuration to allow for stable package standing during storage. At the same time, the legs 407 should not be of a size or dimension that interferes with normal and easy storage of the container 400.

With reference to FIG. 5A, shown is a cross-sectional view of the device 400 of FIG. 5 taken through the center of the container, generally along the plane defined by line D-D. Lid 401 of device 400 is also cutaway in the view of FIG. 5A. FIG. 5A shows an interior mechanism by which a dispensing system functions to provide a user with devices 300 as needed. The internal mechanism includes a spindle 406 which can optionally be placed centrally within the container 400 as shown. The spindle 406 is free to move about its central axis in a rotational fashion. A strip containing a plurality of devices 300 attached together by means of thin filaments 306 and 307 (see FIGS. 4 and 4A) is wound around the spindle. Particularly, the dotted or phantom line indicates the strip containing about fifteen to thirty devices 300 wound around the spindle 406. Again, it will be understood that the number of devices in the strip may vary from this number in the present invention. The winding of devices 300 around the spindle provides a reel of devices 300 that can be conveniently stored and dispensed. As discussed further herein below, the plurality of devices 300 may be stored in the package and other arrangements including stacking on top of one another or other configurations that provide a convenient, preferably sequential, presentation of the devices for use.

Referring now to FIG. 5B, shown is a perspective view of the package of FIG. 5, with lid 401 cut away. An end 301 of a first device 300 is looped through the outlet opening 404 of the container 400. The outlet opening 404 may be of optimal shape and size to allow for the easy passage of the device 300. The outlet opening 404 may be padded with soft material if desired to prevent damage to the device 300 during removal. The location of outlet opening 404 may vary depending upon the location needed to provide efficient mechanical dispensation of devices from the container 400. In the illustrated embodiment, the outlet opening 404 is located on the top right of the container body 402. This provides convenient mechanical action since the devices 300 are wound about the spindle 406 in a counter-clockwise direction in the view presented. If the devices 300 were wound about the spindle in a clockwise direction, the outlet could conveniently be placed on the top left corner of the container body 402 in the view presented. As shown in FIGS. 6A and 6B, the end 301 of a first device 300 is looped through the outlet opening 404 and passed through the cutting element 405. The cutting element 405 may be made of a harder plastic material than that of the device 300, or made of a metal such as steel that is not susceptible to rust. Cutting element 405 may optionally include a knife edge on one of its corners to help the user to separate the device 300 from other devices 300 in the strip at the breakaway notch 309 (see FIG. 5A). When used, the knife or other cutting edge may be placed in such a position where the user intends to separate the devices 300 at the notches 309 of filaments 306 and 307. In this fashion, the knife edge may assist the user in applying the predetermined load to separate the devices at the notch 309 of the filaments 306 and 307. In other embodiments, break assist elements other than knife edges may be used, including for example a cutting element having a serrated edge made, for example, of metal. The design of the cutting or other break assist element will take into consideration the safety of the user to prevent injuries during a separation of device 300 from the strip in which it is contained. In addition, where cutting element 405 is adapted to sever a plastic or other material susceptible to cutting, a plurality of devices may be provided in the strip even where the strip is a continuous or uninterrupted web of material of sufficient length to provide multiple tongue cleaning elements. Thus, breakaway portions or other weakened areas are not necessary in such embodiments of the invention. Preferably, the cutting element is an integral part of the container body 402. In addition, the outlet opening 404 may include an anti-slip mechanism that restricts the device 300 and devices within the container from unintentionally retracting into the body of container 402 whereby they would be inaccessible or only difficulty accessible to the user. Such an anti-slip mechanism may include the creation of friction between the walls or edges of the outlet opening 400 and the strip of devices 300, or other similar friction mechanisms. Further, the spindle mechanism 406 may include a spring mechanism to provide tension on the strip of devices 300 to help in the ease of dispensing and/or preventing retraction of the devices by the user. Suitable spring mechanisms for these purposes are known to those skilled in the art. Where the width of device 300 varies along its length, the design of the outlet and cutting element will take this into account. Further, anti-slip and tension springs on the spindle 406 may help in accommodating such variations while achieving a smooth and convenient dispensing operation.

As discussed above, the lid tab 403 is used to help the user open the lid and to expose the dispensing mechanism. Once the user has successfully removed a device 300, the lid 401 can be closed to protect the remaining devices 300. If desired, the dispensing container or package 400 can be completely or partially made of transparent material to expose the mechanisms of the dispensing system. This may assist the user in determining the quantity of devices remaining for use and whether replenishment is necessary. A closure rim 408 that cooperates with the lid 401 to create a seal, as discussed above, is optional and especially useful in environments that are more susceptible to dust and debris. The lid 401 is optionally hinged to the body 402 and can be hinged either along the long or short axis of the container, as defined by ergonomic or manufacturing needs.

Figure 6:
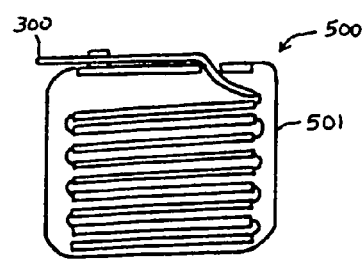
FIG. 6 provides a cutaway view of a package similar to that shown in FIG. 5A, except having therein a stacked, folded configuration for a strip of tongue cleaning devices.
Figure 6A:
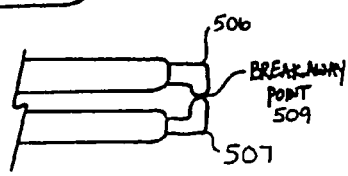
FIG. 6A provides an enlarged view of the breakaway portions of the stacked tongue cleaning devices shown in FIG. 6.

With reference now to FIG. 6, shown is a cross-sectional view of an alternate package 500 for dispensing tongue cleaners of the invention. Package 500 includes a container having an opening and cutting element similar to that of package 400 described hereinabove. However, within package 500 there is contained a strip containing a plurality of devices 300 in a stacked configuration, rather than a wound configuration. In particular, a plurality of devices 300 are interconnected at their ends to one another and stacked in a zigzag or alternating direction fashion within a container 501. To accomplish this stacking, the devices are folded over one another, with the fold-point residing in the filaments 506 and 507 and at the notched area 509. Optionally, filaments 506 and 507 can be manufactured as non-linear elements having a bend or corner therein, as illustrated, to assist in the fold and stacking of the device 300 (see FIG. 6A). It will be understood that package 500 can otherwise contain elements similar to those of package 400, including lids, closures, standing legs, etc.

Figure 7:
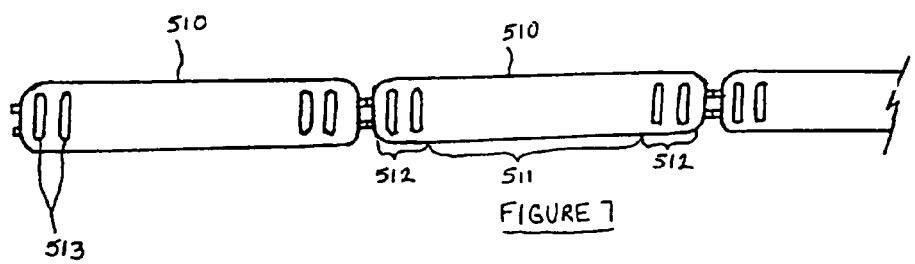
FIG. 7 provides a perspective view of a strip of interconnected tongue cleaning devices similar to that shown in FIG. 4 except having a substantially constant width dimension in the grip and central portions of the devices.

With reference now to FIG. 7, shown is another embodiment of the invention in which a strip containing a plurality of tongue cleaning devices presents devices 510 having a substantially constant height along their length, thus having a substantially constant height among their central portions 511 and handle portions 512. Devices 510 also include proturbences such as protrusions or extrusions 513 on handle portions 512, on at least one face and optionally both faces of the device 510. As shown, devices 510 are interconnected with notched filaments as in previously-described and depicted embodiments.

With reference to FIG. 8, shown is another embodiment of the invention in which a strip of tongue cleaning devices presents a plurality of devices 520 each having a scraping body portion 521 and handle body portion 522 connected to one another at the ends thereof. Scraping body portion 521 includes at least one edge adapted to scrap debris from tongue surfaces, optionally two edges (one on each side), and handle body portion 522 is adapted to serve as a handle during a top to bottom scraping motion of the body portion 521 across the tongue. Body portions 521 and 522 are connected for example by welding or other means at locations such as those depicted at 523, and are also optionally heat welded or otherwise connected to one another along filaments 524 and 525 in which breakaway notch 526 is located.

Handle portion 522 and scraping body portion 521 are designed as flexible elements, wherein handle body portion 522 can be bowed outwardly during a scraping motion, thus increasing the level of curvature in scraping body portion 521 during the scraping motion. As depicted, the periphery of scraping body portion 521 defines a scraping edge 527 that is arcuate. This arcuate edge 527 assists in maintaining contact with the tongue surface across its lateral dimension during the scraping motion. Thus, scraping edge 527 can be adapted to facilitate following the contours of the generally rounded tongue surface to improve the removal of debris from the surface. As illustrated, devices 520 are arranged sequentially and interconnected on the strip. In this fashion, devices 520 can be dispensed from wound or stacked configurations such as those depicted in the prior figures for packages 400 and 500. Strips containing devices 520 can be manufactured in any convenient fashion. In one fashion, separate strips containing a plurality of scraping body portions 521 and handle body portions 522 can be aligned with one another and appropriate connections such as welds made along their length to form a plurality of interconnected devices 520.

With continued reference to FIG. 8, tongue cleaning device of the invention 520 can also be adapted and used as a double-edged tongue scraper, in which body portions 521 and 522 each have at least one edge (and optionally both edges) adapted to scrape tongue surfaces, and the user grips the device 520 at handle portions presented at 523, which handle portions may have surface gripping features as described herein. Body portion 521 would then trail body portion 522 across the tongue during the scraping motion, providing a double scraping function with a single back-to-front pass of the device 520. In this fashion, a more rapid, effective cleaning of tongue surfaces is facilitated. It will be understood that more than two such body portions could also be provided, for example three or four such body portions, to provide more scraping functions per pass of the device. Thus, in general, another embodiment of the invention provides tongue cleaning devices having two or more scraping edges adapted to pass in concert over the tongue during a single pass of the device. Such multi-edge tongue cleaning devices of the invention are desirably, but not necessarily, presented in multiple-device strip form, or in convenient dispensing packages as described herein.

With reference to FIGS. 9, 9A and 9B shown is another package 600 for dispensing tongue cleaning devices of the invention. Package 600 includes a container 601 having a generally rectangular shape. A plurality of tongue cleaning devices 610 are contained within container 601. Devices 610 are similar to those devices depicted in FIG. 7 as 510, except devices 610 are in individual rather than strip form, and do not contain filaments interconnecting them. Container 601 includes an opening 602 for dispensing the tongue cleaning devices 610. Container also includes therein a spring device 603 positioned beneath a stack of devices 610 and adapted to bias the stack upwardly in the container 601. Container 601 has an inner chamber containing the devices 610. The walls of such inner chamber are sufficiently correlated to the dimensions of the exterior perimeter of devices 610 to maintain a relatively orderly stack of devices 610 for dispensing.

With reference now to FIG. 9B, the dispensing adaptations and operation of the package 600 will be more particularly described. Opening 602 includes a first position 604 presenting through the upper surface of container 601 and a second portion 605 presenting through a side wall of container 601. In this fashion, the user may employ a thumb, finger or other implement to initiate contact with the presented device 610 (the uppermost device in the stack in the illustrated embodiment), and apply lateral force to the device 610 to dispense the device 610 laterally through the second (side wall) portion 605 of opening 602. An upper surface 607 of the chamber defined in container 601 is provided at a height which presents the uppermost tongue cleaning device 610 having its lower surface positioned at a level such that lateral dispensing from the container through second (side wall) opening 605 is possible. At the same time, upper surface 607, along with the uppermost device 610, retain the next underlying device 610 at a level wherein an inner surface 606 of a side wall of container 601 protects against any ejection of the underlying device 610 as the uppermost device 610 is dispensed. In the illustrated embodiment, devices 610 contain extrusions, protrusions or other proturbences 611, as in prior-described tongue cleaning devices. These protrusions 611 serve not only for gripping during tongue scraping, but also serve as a friction enhancement during lateral dispensing of the uppermost device 610, and as an effective spacer between devices 610 to improve assurance that underlying devices 610 are positioned sufficiently beneath the uppermost device 610 to contact inner wall surface 606 and thus prevent ejection or dispensing of the underlying device 610 as the uppermost device 610 is dispensed.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A system comprising:
   a) a container unit;
   b) a spool of elongated and flattened tongue scraping strips that are configured to be dispensed from an outlet opening of the container unit, wherein each elongated and flattened tongue scraping strip within the set of elongated and flattened tongue scraping strips has at least one elongated tongue scraping edge; and are detachably coupled to each other and
   c) an anti-slip mechanism that provides tension on each elongated and flattened tongue scraping strip as each elongated and flattened tongue scraping strip is dispensed from the outlet opening of the container unit.

2. The system of claim 1, wherein the container includes a cutting feature for separating tongue scraping strips.

3. The system of claim 1, wherein the elongated and flattened tongue scraping strips are concentrically position around a spool.

4. The system of claim 1, wherein the elongated and flattened tongue scraping strips includes a bowed elongated and flattened scraping strip and a handle strip that is coupled ends of the bowed elongated and flattened scraping strip.

5. The system of claim 1, wherein the elongated and flattened tongue scraping strips are separated through break away tabs.

6. The system of claim 1, wherein the one or more ends of the elongated and flattened tongue scraping strips include widened handle portions for holding the ribbons or strips after being separated.

7. The system of claim 6, wherein the widened handle portions are textured.

8. The system of claim 1, wherein the container unit comprises a traction feature for providing resistance to elongated and flattened tongue scraping strips as the elongated and flattened tongue scraping strips are being dispensed from the container.

9. The system of claim 1, wherein the elongated and flattened tongue scraping strips are formed from one or more of a plastic or metal material.

10. The system of claim 9, wherein the elongated and flattened tongue scraping strips are coated with a film.

11. The system of claim 10, wherein the film includes a flavoring agent.

12. A system comprising:
   a) tongue scraping strips configured to be individually dispensed from an opening of a container, wherein each of the tongue scraping strips within the set of tongue scraping strips comprises an elongated flattened tongue scraping portion with at least one elongated tongue scraping edge, and wherein the set of tongue scraping strips are stacked in a layered fashion within the container; and
   b) a spring member position on a bottom portion of the container for urging the tongue scraping strips to a top portion of the container, such that at least one of the tough scraping strips is aligned with the opening of the container.

13. The system of claim 12, wherein the tongue scraping strips include handle portions positioned at opposed ends of the tongue scraping strips.

14. The system of claim 13, wherein the handle portions of the tongue scraping strips are wider than the tongue scraping portions of the tongue scraping strips.

15. The system of claim 13, wherein the handle portions of the tongue scraping strips are textured.

16. The system of claim 12, wherein the tongue scraping portions of the tongue scraping strips are bowed or curved.

17. The system of claim 12, wherein the tongue scraping strips are formed from one or more of a plastic or a metal material.

18. The system of claim 12, wherein a portion of the tongue scraping strips are coated with a film comprising a flavoring agent.

19. A system comprising:
a) a container with a slotted feature; and
b) a spool of elongated and flattened tongue scraping strips with elongated tongue scraping edges, wherein the elongated and flattened tongue scraping strips are configured to be dispensed from the slotted feature of the container, and wherein consecutive elongated and flattened tongue scraping strips within the spool of elongated and flattened tongue scraping strips are separable through break away tabs or perforations and wherein the flattened tongue scraping strips are impregnated or coated with a flavoring and have structural integrity required to scrape a user's tongue without folding or collapsing.

\* \* \* \* \*